United States Patent [19]

Mitamura et al.

[11] Patent Number: 4,975,275

[45] Date of Patent: Dec. 4, 1990

[54] HAIR CONDITIONING COMPOSITIONS

[75] Inventors: Joji Mitamura, Tokyo; Hideo Kurokawa, Machida, both of Japan

[73] Assignee: Lion Corporation, Tokyo, Japan

[21] Appl. No.: 441,554

[22] Filed: Nov. 27, 1989

[30] Foreign Application Priority Data

Dec. 19, 1988 [JP] Japan ................................ 63-320075

[51] Int. Cl.$^5$ .............................................. A61K 7/075
[52] U.S. Cl. ....................................... 424/70; 514/788

[58] Field of Search .................. 424/70; 514/788, 634; 564/230, 240

Primary Examiner—Merrell C. Cashion, Jr.
Assistant Examiner—Susan S. Rucker
Attorney, Agent, or Firm—Birch, Stewart, Kolasch & Birch

[57] ABSTRACT

A hair conditioning composition comprising a guanidine derivative having an amide group in its molecule or a salt thereof as an active ingredient is effective to render damaged hair soft and moist.

17 Claims, No Drawings

HAIR CONDITIONING COMPOSITIONS

This invention relates to a hair conditioning composition containing an active ingredient which is well adsorbed to the hair to impart improved softness and humectation to the hair.

BACKGROUND OF THE INVENTION

In general, hairs are covered with sebum or the like secreted by themselves. Shampooing with detergents, soaps or the like and permanent waving cause the sebum to be removed more than the necessary. Due to a loss of smoothness, the shampooed or permed hair is dry, loose and hard in feel and difficult to comb, tending to split. To eliminate such inconvenience resulting from removal of sebum, a variety of hair care products have been developed as hair conditioners. Known hair care products typically contain as the active ingredient a quaternary ammonium salt, for example, a di-long chain, di-short chain alkyl ammonium salt such as dialkyl dimethyl ammonium chloride or a mono-long chain alkyl, tri-short chain alkyl ammonium salt such as alkyl trimethyl ammonium chloride.

However, these quaternary ammonium salts are not only stimulative to the hair and scalp, but also tend to leave the hair upon rinsing because they have a weak force of adsorption to the hair as a result of the steric hindrance that the charged nitrogen atom playing the role of an adsorption center is surrounded by long and short chain alkyl or alkenyl groups. Hair care products containing such a quaternary ammonium salt as the active ingredient need further improvements in imparting softness and smoothness to the shampooed hair because the active ingredient is insufficiently adsorbed to the hair. There is a need for the development of a hair care product containing an active ingredient which is sufficiently adsorbed to the hair to eliminate any inconvenience as experienced after shampooing or permanent waving.

SUMMARY OF THE INVENTION

Therefore, an object of the present invention is to provide a novel and improved hair conditioning composition containing an active ingredient which is well adsorbed to the hair to render the hair soft and moist.

According to the present invention, there is provided a hair conditioning composition comprising as an active ingredient at least one member selected from the class consisting of a guanidine derivative having an amide group in its molecule represented by the general formula:

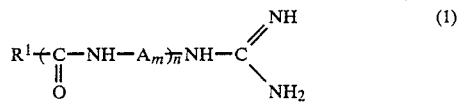

wherein $R^1$ is selected from linear and branched alkyl and alkenyl groups having 1 to 22 carbon atoms, A is selected from linear and branched alkylene and alkenylene groups having 1 to 10 carbon atoms, letter m is equal to 0 or 1, and n is an integer of 1 to 5, and a salt thereof. This active ingredient is well adsorbed to the hair so that the hair may become soft and retain moisture.

A mono-N-substituted guanidine derivative has a guanidine group, that is, a strongly basic group in the molecule, which possesses a strong electrostatic effect capable of forming a strong dipolar ion with a resonance type monovalent anion species such as a carboxy anion as well as a hydrogen bonding ability. Thus the guanidine derivative has a high affinity to fibrous proteins such as keratin having a resonance type monovalent anion species at a terminal side chain and form a dipolar ion with said anion species, presenting strong adsorptive forces. The derivative of formula (1) which is obtained by introducing an amide group into the substituent of the mono-N-substituted guanidine derivative exhibits a very high affinity to fibrous proteins such as keratin and well sticks to the hair to impart improved softness to the hair. Since the amide group introduced provides the derivative of formula (1) with an increased ability of fixing water molecules, the derivative is effective to impart humidity retention to the hair. Because of its molecular structure, the derivative of formula (1) has high absorptivity to the hair which has been rendered hydrophilic through permanent wave treatment or the like so that it is well adsorbed to not only normal hair after shampooing, but also to damaged hair after permanent wave treatment or the like, imparting softness and humectation to the hair. In this way, the inconvenience resulting from excess removal of sebum by shampooing and permanent waving treatments is solved. That is, the derivative of formula (1) is a satisfactory active ingredient for hair conditioning.

DETAILED DESCRIPTION OF THE INVENTION

The hair conditioning composition of the invention contains a guanidine derivative having an amide group in its molecule represented by the general formula:

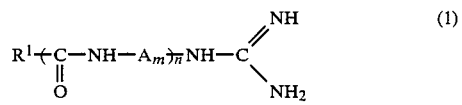

or a salt thereof as an active ingredient.

In formula (1), $R^1$ is selected from linear and branched alkyl and alkenyl groups having 1 to 22 carbon atoms, preferably 11 to 19 carbon atoms. Preferred non-limiting examples include $C_{11}H_{23}$—, $C_{12}H_{25}$—, $C_{13}H_{27}$—, $C_{14}H_{29}$—, $C_{15}H_{31}$—, $C_{16}H_{33}$—, $C_{17}H_{35}$, $(C_8H_{17})CH$—, and $4-C_2H_5C_{15}H_{30}$—.

Substituent A is selected from linear and branched alkylene and alkenylene groups having 1 to 10 carbon atoms, preferably 2 to 6 carbon atoms. Preferred non-limiting examples include a methylene group, ethylene group, propylene group, butylene group, pentylene group, hexylene group, isopropylene group, 2-pentenyl group, and 2-ethylbutylene group.

Letter m is equal to 0 or 1, and n is an integer having a value of from 1 to 5.

Often, the guanidine derivative of formula (1) is blended in the composition in the form of a salt. Examples of the salt include inorganic acid salts such as salts of hydrochloric acid, nitric acid, hydrobromic acid, hydroiodic acid, orthophosphoric acid, and perchloric acid, and organic acid salts such as salts of glycolic acid, acetic acid, citric acid, dimethylsulfuric acid, diethylsulfuric acid, malic acid, and acidic amino acids. The hydrochloride salts are preferred among the inorganic acid salts and the glycolates are preferred among the organic acid salts, both for their solubility in water.

The guanidine derivatives of formula (1) and salts thereof may be blended in the composition alone or in admixture of two or more. The amount of the derivative or salt blended is not particularly limited although it is often in the range of about 0.05 to about 10% by weight, especially about 0.7 to about 5% by weight of the composition. Less than 0.05% by weight of the active ingredient would be less effective in imparting softness. With more than 10% by weight of the active ingredient, the composition would be uneconomical and rather give a sticky heavy finish.

The hair conditioning compositions of the invention may be prepared as hair rinses, spray or dispenser type hair conditioners, hair treatments, hair lotions or the like. The compositions may be prepared in any desired product form including solution, homogeneous dispersion, heterogeneous dispersion, and emulsion.

Most often, the hair conditioning compositions of the invention contain, in addition to the active ingredient, any suitable additives depending on their intended purpose, application, and form. For example, there may be additionally blended alcohols, especially higher alcohols having 14 to 20 carbon atoms such as cetanol, stearyl alcohol, cetostearyl alcohol, and isocetanol, typically in an amount of 1 to 5% by weight; silicone oils such as dimethylpolysiloxane and other oily values, typically in an amount of 0 to 10% by weight, especially 0.1 to 10% by weight; nonionic surface-active agents such as polyoxyethylene derivatives including polyoxyethylene-added hardened castor oil triisostearate, sorbitan monostearate, typically in an amount of 0.05 to 10% by weight; cationic surface-active agents such as stearyl trimethyl ammonium chloride and distearyl dimethyl ammonium chloride, typically in an amount of 0 to 5% by weight, especially 0.05 to 5% by weight; amino acids such as glycine, aspartic acid, and glutamic acid, typically in an amount of 0 to 5% by weight, especially 0.1 to 5% by weight; as well as solvents, emulsifiers, humectants, dandruff removers, antioxidants, chelating agents, UV absorbers, perfumes, coloring agents and other additives commonly used in conventional hair care products. The amounts of these additives blended are not particularly limited and may be determined according to the conventional practice without undue experimentation. Other optional additives include ester oils, hydrolyzed proteins, and anionic surface-active agents such as lauryl ether sulfate, each typically blended in amounts of 0 to 5% by weight, especially 0.1 to 5% by weight.

There has been described a hair conditioning composition having a guanidine derivative of formula (1) or a salt thereof blended as an active ingredient. The sorption of the active ingredient to the hair is increased so that the hair treated with the composition becomes fully soft and retains moisture. The composition is effective in rendering soft and smooth the hair having a dry, loose, and hard feel as a result of excess removal of sebum by shampooing and permanent wave treatments.

EXAMPLE

Examples of the present invention are given below by way of illustration and not by way of limitation. All percents are by weight unless otherwise stated.

Experiments are first given to show the effectiveness of the active ingredient of the present invention.

Experiment 1

Bundles of hairs were used each weighing 10 grams and 20 cm long. A bundle of normal hairs was prepared by washing with an anionic surface-active agent.

The bundle of normal hairs was immersed for 7 minutes in a 5% ammonium thioglycolate bath at pH 9.6 in a weight ratio of hair to bath of 1:30. The hair bundle was washed with water, and again immersed for 10 minutes in a 3% potassium bromate bath in a weight ratio of hair to bath of 1:40. The hair bundle was fully washed with water and air dried, obtaining a bundle of damaged hairs, that is, cold wave hairs.

A test was conducted on the normal hair bundles and the damaged hair bundles by applying 1.0 gram of a solution containing 1.0% of the active ingredient shown in Table 1 to the hair and fully combing the hair. The hair bundles were rinsed 2, 4 and 8 cycles, each cycle consisting of shaking 5 times up and down in 250 ml of warm water at 40° C. The ingredient left in each hair bundle after rinsing was extracted with a Soxhlet's extractor using ethanol solvent. After vacuum distillation of the ethanol, the remaining ingredient was quantitatively determined by high performance liquid chromatography according to the absolute calibration curve method.

The results are shown in Table 1. The amount of remaining ingredient is reported as an average of four measurements.

TABLE 1

|  | Active Ingredient | Normal Hair Bundle Rinsing Cycles | | | Damaged Hair Bundle Rinsing Cycles | | |
|---|---|---|---|---|---|---|---|
|  |  | 2 | 4 | 8 | 2 | 4 | 8 |
| Invention | Guanidine derivative salt $C_{11}H_{23}C(=O)-N(H)-C_6H_{12}NHC(=NH)(NH_2) \cdot HCl$ | 8.5 mg | 8.1 mg | 7.2 mg | 9.3 mg | 9.1 mg | 8.6 mg |
|  | $C_{13}H_{27}C(=O)-N(H)-C_4H_8NHC(=NH)(NH_2) \cdot HCl$ | 8.5 | 8.0 | 7.2 | 9.3 | 9.0 | 8.7 |
|  | $C_{15}H_{31}C(=O)-N(H)-C_2H_4NHC(=NH)(NH_2) \cdot HCl$ | 8.7 | 8.4 | 7.5 | 9.5 | 9.2 | 8.8 |

TABLE 1-continued

| | Active Ingredient | | Normal Hair Bundle Rinsing Cycles | | | Damaged Hair Bundle Rinsing Cycles | | |
|---|---|---|---|---|---|---|---|---|
| | | | 2 | 4 | 8 | 2 | 4 | 8 |
| | $C_{17}H_{35}\underset{O}{\overset{\parallel}{C}}-\underset{H}{N}-C_2H_4NHC\overset{\nearrow NH}{\underset{\searrow NH_2}{}}\cdot HCl$ | | 9.0 | 8.9 | 8.1 | 9.6 | 9.4 | 8.9 |
| | $C_{17}H_{35}\underset{O}{\overset{\parallel}{C}}-\underset{H}{N}-C_3H_6NHC\overset{\nearrow NH}{\underset{\searrow NH_2}{}}\cdot HCl$ | | 9.0 | 8.8 | 8.2 | 9.6 | 9.5 | 8.9 |
| Comparison | Quaternary ammonium salt | $C_{12}H_{25}N^{\oplus}(CH_3)_3Cl^{\ominus}$ | 6.0 | 4.7 | 4.0 | 6.5 | 5.1 | 4.1 |
| | | $C_{18}H_{37}N^{\oplus}(CH_3)_3Cl^{\ominus}$ | 7.3 | 6.0 | 4.7 | 8.0 | 6.3 | 5.0 |

As seen from the data of Table 1, the salts of guanidine derivatives having an amide group were well adsorptive to hair in that, as compared with the prior art quaternary ammonium salts, said salts remained adsorbed to the normal hair in an increased amount at the initial (after 2 cycles of rinsing), and experienced a less reduction in the retention amount on the hair even after repeated cycles of rinsing.

The prior art quaternary ammonium salts remained adsorbed to the damaged hair (cold wave hair) in a more amount than to the normal hair (washed hair) at the initial, but tended to leave more the damaged hair as the rinsing cycle was repeated, the retention amount on the damaged hair being approximately equal to that on the normal hair after 8 cycles of rinsing. In contrast, the guanidine derivative salts were adsorbed to the damaged hair in an increased amount at the initial and remained well adsorbed to the damaged hair even after the repeated cycles of rinsing.

It is thus evident that the guanidine derivative salts show not only high adsorption to the normal hair, but also fast adsorption to the damaged hair which has been changed into more hydrophilic fibrous protein by a cold wave or similar damaging treatment.

Although most commercially available rinses and treatments specially intended for the treatment of damaged hair after shampooing and permanent wave contain quaternary ammonium salts as the major active ingredient, the guanidine derivative salts defined herein are found to be an effective substitute for the quaternary ammonium salts as an active ingredient of a hair conditioning composition for damaged hair.

Experiment 2

A normal hair bundle washed as in Experiment 1 was treated by applying a solution containing 1.0% of the active ingredient shown in Table 2, rinsing 2 cycles, and air drying. After air drying, those hairs having longer and shorter diameters in the range between 60 μm and 80 μm approximating to a cylindrical shape were selected from the hair bundle. 100 hairs at opposed ends were adhesively attached to 12-mm spaced apart paper pieces having a width of 40 mm and a length of 52 mm at longitudinal spacings of 0.5 mm. Using a model KFS-FB2 bending tester, the array of hairs was measured for bending stiffness at the relative humidity (RH) shown in Table 2.

The results are shown in Table 2. The bending stiffness is an average of four measurements.

TABLE 2

| | Active Ingredient | | Bending Stiffness at | | | |
|---|---|---|---|---|---|---|
| | | | RH 40% | RH 60% | RH 80% | RH 90% |
| Invention | Guanidine derivative salt | $C_{11}H_{23}\underset{O}{\overset{\parallel}{C}}-\underset{H}{N}-C_6H_{12}NHC\overset{\nearrow NH}{\underset{\searrow NH_2}{}}\cdot HCl$ | 0.63 | 0.71 | 0.80 | 0.80 |
| | | $C_{15}H_{31}\underset{O}{\overset{\parallel}{C}}-\underset{H}{N}-C_2H_4NHC\overset{\nearrow NH}{\underset{\searrow NH_2}{}}\cdot HCl$ | 0.63 | 0.70 | 0.80 | 0.80 |
| | | $C_{17}H_{35}\underset{O}{\overset{\parallel}{C}}-\underset{H}{N}-C_2H_4NHC\overset{\nearrow NH}{\underset{\searrow NH_2}{}}\cdot HCl$ | 0.65 | 0.72 | 0.80 | 0.80 |
| | | $C_{11}H_{23}-\left(\underset{O}{\overset{\parallel}{C}}-\underset{H}{N}-C_2H_4\right)_2-NHC\overset{\nearrow NH}{\underset{\searrow NH_2}{}}\underset{COOH}{\overset{OH}{\underset{|}{CH_2}}}$ | 0.64 | 0.75 | 0.80 | 0.80 |

TABLE 2-continued

| Active Ingredient | | Bending Stiffness at | | | |
|---|---|---|---|---|---|
| | | RH 40% | RH 60% | RH 80% | RH 90% |
| | $C_{13}H_{27}\text{---}\left(\underset{\underset{O}{\parallel}}{C}\text{---}\underset{H}{N}\text{---}C_2H_4\right)_2\text{---}NHC\overset{\overset{NH}{\parallel}}{\underset{NH_2}{\diagdown}}\overset{OH}{\underset{COOH}{\overset{\mid}{CH_2}}}$ | 0.66 | 0.74 | 0.80 | 0.80 |
| Comparison | Alkyl guanidine $C_{12}H_{25}NHC\overset{NH}{\underset{NH_2}{\diagdown}}\cdot HCl$ | 0.58 | 0.69 | 0.79 | 0.79 |
| | Quaternary ammonium salt $C_{18}H_{37}N^{\oplus}(CH_3)_3Cl^{\ominus}$ | 0.56 | 0.65 | 0.79 | 0.79 |
| | Control (untreated) | 0.52 | 0.61 | 0.70 | 0.75 |

As seen from the data of Table 2, the hairs treated with the salts of guanidine derivatives having an amide group showed a lower bending stiffness than the control hair (untreated) and those treated with the alkyl guanidine hydrochloride and quaternary ammonium salt.

The hairs in the holder zone were measured for surface moisture by means of a near-infrared surface moisture meter.

The results are shown in Table 3. The coefficient of surface moisture is an average of three measurements.

TABLE 3

| | Active Ingredient | Coefficient of Surface Moisture at | | | |
|---|---|---|---|---|---|
| | | RH 40% | RH 60% | RH 80% | RH 90% |
| Invention | Guanidine derivative salt $C_{11}H_{23}\underset{\underset{O}{\parallel}}{C}\text{---}\underset{H}{N}\text{---}C_6H_{12}NHC\overset{NH}{\underset{NH_2}{\diagdown}}\cdot HCl$ | 0.63 | 0.71 | 0.80 | 0.80 |
| | $C_{15}H_{31}\underset{\underset{O}{\parallel}}{C}\text{---}\underset{H}{N}\text{---}C_2H_4NHC\overset{NH}{\underset{NH_2}{\diagdown}}\cdot HCl$ | 0.63 | 0.70 | 0.80 | 0.80 |
| | $C_{17}H_{35}\underset{\underset{O}{\parallel}}{C}\text{---}\underset{H}{N}\text{---}C_2H_4NHC\overset{NH}{\underset{NH_2}{\diagdown}}\cdot HCl$ | 0.65 | 0.72 | 0.80 | 0.80 |
| | $C_{11}H_{23}\text{---}\left(\underset{\underset{O}{\parallel}}{C}\text{---}\underset{H}{N}\text{---}C_2H_4\right)_2\text{---}NHC\overset{\overset{NH}{\parallel}}{\underset{NH_2}{\diagdown}}\overset{OH}{\underset{COOH}{\overset{\mid}{CH_2}}}$ | 0.64 | 0.75 | 0.80 | 0.80 |
| | $C_{13}H_{27}\text{---}\left(\underset{\underset{O}{\parallel}}{C}\text{---}\underset{H}{N}\text{---}C_2H_4\right)_2\text{---}NHC\overset{\overset{NH}{\parallel}}{\underset{NH_2}{\diagdown}}\overset{OH}{\underset{COOH}{\overset{\mid}{CH_2}}}$ | 0.66 | 0.74 | 0.80 | 0.80 |
| Comparison | Alkyl guanidine $C_{12}H_{25}NHC\overset{NH}{\underset{NH_2}{\diagdown}}\cdot HCl$ | 0.58 | 0.69 | 0.79 | 0.79 |
| | Quaternary ammonium salt $C_{18}H_{37}N^{\oplus}(CH_3)_3Cl^{\ominus}$ | 0.56 | 0.65 | 0.79 | 0.79 |
| | Control (untreated) | 0.52 | 0.61 | 0.70 | 0.75 |

That is, the guanidine derivative salts were found to be more effective in softening hairs.

Experiment 3

A bundle of hairs treated as in Experiment 2 was adjusted to a relative humidity as shown in Table 3 and then disintegrated. Two divided groups of hairs each group having a transverse distance of 4 cm were laid at an intersection angle of 90°. The intersection was secured by a holder having a circular 4-cm diameter hole.

As seen from the data of Table 3, the hairs treated with the salts of guanidine derivatives having an amide group showed an equivalent coefficient of surface moisture in high humidity conditions, but a higher coefficient of surface moisture in low humidity conditions, as compared with the control hair (untreated) and those treated with the alkyl guanidine hydrochloride and quaternary ammonium salt. That is, the guanidine derivative salts were found to be more effective in fixing water even in low humidity conditions and thus rendering hair moist.

Examples are presented below. In the formulations, POE is an abbreviation of polyoxyethylene.

EXAMPLE 1

A hair rinse composition was prepared according to the following formulation:

| | |
|---|---|
| Guanidine derivative salt | 0.7% |
| $C_{17}H_{35}\underset{O}{\underset{\parallel}{C}}-NH-C_2H_4-NHC\underset{NH_2}{\overset{NH}{\diagup\!\!\!\diagdown}}\cdot HCl$ | |
| Cetanol/stearyl alcohol (1/1 by volume) | 2.5% |
| POE (30 mol) glyceryl monoisostearate | 1.0% |
| Propylene glycol | 7.0% |
| Perfume | 0.5% |
| Purified water | balance |
| Total | 100.0% |

For comparison purposes, another hair rinse composition was prepared having the same formulation as above except that the guanidine derivative salt was replaced by stearyl trimethyl ammonium chloride. A panel of 10 women made an organoleptic examination of these two hair rinse compositions for feel and finish upon application. Six panel members among ten favored the guanidine derivative salt-containing composition for its feel upon application.

EXAMPLE 2

A hair rinse composition was prepared according to the following formulation:

| | |
|---|---|
| Guanidine derivative salt | 0.8% |
| $C_{11}H_{23}-(\underset{O}{\underset{\parallel}{C}}-NH-C_2H_4)_2-NHC\underset{NH_2\;COOH}{\overset{NH\quad OH}{\diagup\!\!\!\underset{\mid}{CH_2}}}\cdot$ | |
| Cetanol/stearyl alcohol (1/1 by volume) | 2.5% |
| Sorbitan sesquioleate | 1.0% |
| Dimethylpolysiloxane (500 centistokes) | 1.5% |
| Isopropyl palmitate | 0.4% |
| POE (30 mol) hardened castor oil stearate | 0.7% |
| Perfume | 0.5% |
| Purified water | balance |
| Total | 100.0% |

A panel of 15 women made an organoleptic examination of the rinse composition. Ten panel members among fifteen appreciated the composition as giving a smooth finish and a gently moist feel to the hair.

EXAMPLE 3

A hair treatment composition was prepared according to the following formulation:

| | |
|---|---|
| Guanidine derivative salt | 1.0% |
| $C_{13}H_{27}-(\underset{O}{\underset{\parallel}{C}}-NH-C_2H_4)_2-NHC\underset{NH_2\;COOH}{\overset{NH\quad OH}{\diagup\!\!\!\underset{\mid}{CH_2}}}$ | |
| Guanidine derivative salt | 0.8% |
| $C_{17}H_{35}\underset{O}{\underset{\parallel}{C}}-NH-C_2H_4-NHC\underset{NH_2}{\overset{NH}{\diagup\!\!\!\diagdown}}\cdot HCl$ | |
| Cetanol/stearyl alcohol (3/7 by volume) | 3.0% |
| Lanolin | 0.5% |
| POE lauryl ether sulfite | 0.2% |
| POE (30 mol) hardened castor oil triisostearate | 1.0% |
| POE (25 mol) trimethylolpropane isostearate | 0.5% |
| POE (40 mol) nonylphenyl ether | 0.15% |
| Perfume | 0.5% |
| Purified water | balance |
| Total | 100.0% |

For comparison purposes, another hair treatment composition was prepared having the same formulation as above except that the guanidine derivative salt was replaced by stearyl trimethyl ammonium chloride. A panel of 20 women made an organoleptic examination of these compositions. Fourteen panel members among twenty favored the guanidine derivative salt-containing composition for its application feel, with eight members among the fourteen giving the best evaluation point for its feel.

EXAMPLE 4

A hair conditioner was prepared according to the following formulation:

| | |
|---|---|
| Stearyl trimethyl ammonium chloride | 0.5% |
| $C_{17}H_{35}-\underset{O}{\underset{\parallel}{C}}-NH-C_2H_4-NHC\underset{NH_2}{\overset{NH}{\diagup\!\!\!\diagdown}}\cdot HCl$ | 0.5% |
| Cetostearyl alcohol | 4.0% |
| Polypropylene glycol (20 mol) sorbitol ether | 2.0% |
| Glycine | 1.0% |
| Sorbitan monostearate | 0.7% |
| POE (20 mol) glyceryl triisostearate | 1.5% |
| Purified water | balance |
| Total | 100.0% |

EXAMPLE 5

A hair treatment composition was prepared according to the following formulation:

| | |
|---|---|
| Distearyl dimethyl ammonium chloride | 1.0% |
| $C_{17}H_{35}-\underset{O}{\underset{\parallel}{C}}-NH-C_2H_4-NHC\underset{NH_2}{\overset{NH}{\diagup\!\!\!\diagdown}}\cdot HCl$ | 0.5% |
| Cetostearyl alcohol | 5.0% |
| Dimethylpolysiloxane ($10^5$ centistokes) | 3.0% |
| Hydrolyzed collagen peptide | 1.0% |
| Myristyl octyl dodecanate | 1.0% |
| Purified water | balance |
| Total | 100.0% |

Although some preferred embodiments have been described, many modifications and variations may be

We claim:

1. A hair conditioning composition comprising as an active ingredient at least one member selected from the class consisting of a guanidine derivative having an amide group in its molecule represented by the general formula:

$$R^1 \!-\!\!\left(\!C(=O)\!-\!NH\!-\!A_m\!\right)_{\!n}\!NH\!-\!C(=NH)\!-\!NH_2 \quad (1)$$

wherein $R^1$ is selected from linear and branched alkyl and alkenyl groups having 1 to 22 carbon atoms, A is selected from linear and branched alkylene and alkenylene groups having 1 to 10 carbon atoms, letter m is equal to 0 or 1, and n is an integer of 1 to 5, and a salt thereof.

2. The composition of claim 1, comprising a salt of a guanidine derivative of formula (1).

3. The composition of claim 2 wherein said salt is a hydrochloride salt.

4. The composition of claim 2 wherein said salt is a glycolate salt.

5. The composition of any one of claims 1 to 4 wherein the guanidine derivative of formula (1) or the salt thereof is present in an amount of 0.05 to 10% by weight of the composition.

6. The composition of claim 1, wherein $R^1$ is selected from linear and branched alkyl and alkenyl groups having 11 to 19 carbon atoms.

7. The composition of claim 1, wherein $R^1$ is selected from the group consisting of $C_{11}H_{23}-$, $C_{12}H_{25}-$, $C_{13}H_{27}-$, $C_{14}H_{29}-$, $C_{15}H_{31}-$, $C_{16}H_{33}-$, $C_{17}H_{35}-$, $(C_8H_{17})CH-$ and $4-C_2H_5C_{15}H_{30}-$.

8. The composition of claim 1, wherein A is selected from linear and branched alkylene and alkenylene groups having 2 to 6 carbon atoms.

9. The composition of claim 1, wherein A is selected from the group consisting of a methylene group, ethylene group, propylene group, butylene group, pentylene group, hexylene group, isopropylene group, 2-pentenyl group, and 2-ethyl-butylene group.

10. The composition of claim 3, wherein $R^1$ is selected from the group consisting of $C_{11}H_{23}-$, $C_{12}H_{25}-$, $C_{13}H_{27}-$, $C_{14}H_{29}-$, $C_{15}H_{31}-$, $C_{16}H_{33}-$, $C_{17}H_{35}-$, $(C_8H_{17})CH-$ and $4-C_2H_5C_{15}H_{30}-$ and wherein A is selected from the group consisting of a methylene group, ethylene group, propylene group, butylene group, pentylene group, hexylene group, isopropylene group, 2-pentenyl group, and 2-ethyl-butylene group.

11. The composition of claim 4, wherein $R^1$ is selected from the group consisting of $C_{11}H_{23}-$, $C_{12}H_{25}-$, $C_{13}H_{27}-$, $C_{14}H_{29}-$, $C_{15}H_{31}-$, $C_{16}H_{33}-$, $C_{17}H_{35}-$, $(C_8H_{17})CH-$ and $4-C_2H_5C_{15}H_{30}-$ and wherein A is selected from the group consisting of a methylene group, ethylene group, propylene group, butylene group, pentylene group, hexylene group, isopropylene group, 2-pentenyl group, and 2-ethyl-butylene group.

12. The composition of claim 5, wherein the guanidine derivative of formula (1) or the salt thereof is present in an amount of 0.7 to about 5% by weight of the composition.

13. The composition of claim 1, wherein the guanidine derivative of formula (1) is $$C_{17}H_{35}C(=O)-N(H)-C_2H_4NHC(=NH)-NH_2 \cdot HCl.$$

14. The composition of claim 1, wherein the guanidine derivative of formula (1) is $$C_{13}H_{27}-\!\!\left[C(=O)-N(H)-C_2H_4\right]_{\!2}\!-NHC(=NH)-NH_2 \cdot CH_2(OH)COOH.$$

15. The composition of claim 1, wherein the guanidine derivative of formula (1) is $$C_{11}H_{22}C(=O)-N(H)-C_6H_{12}NHC(=NH)-NH_2 \cdot HCl.$$

16. The composition of claim 1, wherein the guanidine derivative of formula (1) is $$C_{11}H_{23}-\!\!\left[C(=O)-N(H)-C_2H_4\right]_{\!2}\!-NHC(=NH)-NH_2 \cdot CH_2(OH)COOH.$$

17. The composition of claim 1, wherein the guanidine derivative of formula (1) is $$C_{15}H_{31}C(=O)-N(H)-C_2H_4NHC(=NH)-NH_2 \cdot HCl.$$

* * * * *